| United States Patent [19] | [11] Patent Number: 4,542,254 |
| Santacesaria et al. | [45] Date of Patent: Sep. 17, 1985 |

[54] PROCESS FOR THE SEPARATION OF MIXTURES OF AROMATIC HYDROCARBONS INTO SINGLE COMPONENTS

[75] Inventors: Elio Santacesaria; Franco Codignola, both of Milan; Davino Gelosa, Pavia; Sergio Carra', Milan, all of Italy

[73] Assignee: Sisassocieta Italianaserie Acetica Sintetica, Milan, Italy

[21] Appl. No.: 491,229

[22] Filed: May 3, 1983

[30] Foreign Application Priority Data

May 4, 1982 [IT] Italy ................................ 21059 A/82

[51] Int. Cl.[4] .......................... C10G 25/03; C07C 7/12
[52] U.S. Cl. .................................. 585/828; 208/310 Z
[58] Field of Search ..................... 208/310 Z; 585/828

[56] References Cited

U.S. PATENT DOCUMENTS

| 3,686,342 | 8/1972 | Neuzil | 208/310 Z X |
| 3,734,974 | 5/1973 | Neuzil | 208/310 Z X |
| 3,855,333 | 12/1974 | Neuzil | 208/310 Z X |
| 3,943,182 | 3/1976 | Neuzil et al. | 208/310 Z X |
| 4,079,094 | 3/1978 | Rosback et al. | 208/310 Z X |
| 4,368,347 | 1/1983 | Carra et al. | 208/310 Z X |

*Primary Examiner*—D. E. Gantz
*Assistant Examiner*—Glenn Caldarola
*Attorney, Agent, or Firm*—Cushman, Darby & Cushman

[57] ABSTRACT

There is provided a process for the separation of aromatic hydrocarbons mixtures into single components, in which the mixtures in vapor phase pass onto an adsorption bed formed by a potassium-exchanged Y zeolite, which is preventively saturated with desorbent vapors. According to the invention the desorbent used is isopropylbenzene in vapor phase. This facilitates the quick separation of the pure components, with the exception of the presence of desorbent. The process according to this invention is quicker in comparison to traditional ones. It requires the use of lower charges of desorbent and allows the separation of single pure components of the mixtures. It especially improves the paraxylene separation in higher concentrations with respect to the desorbent.

8 Claims, 12 Drawing Figures

PROCESS FOR THE SEPARATION OF MIXTURES OF AROMATIC HYDROCARBONS INTO SINGLE COMPONENTS

BACKGROUND OF THE INVENTION

This invention concerns a process for the separation of aromatic hydrocarbon mixtures into single components.

The ortho, para, metaxylene and ethylbenzene $C_8$ isomers, in condition, are used industrially as raw materials for the production of various petrochemicals which, in turn, are used to prepare plastics, resins and other things. It is well known that the separation of the individual isomers from their mixtures is a very difficult operation, because of the proximity of the boiling points and because of the similarity of the other chemical-physical characteristics.

More recently, the separation of these isomers fulfilled has been accomplished through selective adsorption on zeolite-type materials. Such a separation can be theoretically considered as a two-stage process: an adsorption stage, where a part of the components of the $C_8$ fraction is fixed on the zeolite material, thus undergoing a first separation; and a desorption stage, where the product fixed on the zeolite is separated by adding another component (desorbent) which has a greater affinity for the zeolite compared to that of the adsorbed material. Of the two steps, the desorption one is usually slower and therefore affects the rate of the total process.

In U.S. Pat. No. 3,773,846 there is disclosed a process for the separation on zeolite of meta- and paraxylene from a liquid fraction of $C_8$ aromatic compounds. In such a process the desorbent used is any one of the xylene fractionation products, preferably toluene or diethylbenzene. It is important to emphasize that in the process described in that patent, the products used as desorbent are reputed to be fully equivalent and accordingly are not important. However, as will be pointed out below, toluene is not especially suitable to desorb the components being fixed on the zeolite. Ethylbenzene cannot in turn be separated from the other isomers.

Hence, there is no need to take advantage of a complicated series of traditional operations, such as fractional crystallization and so on.

In Italian patent application No. 24044 A/80 there is disclosed the use of type Y zeolite material having large pores exchanged with potassium.

The so treated materials absorbs the paraxylene very well and the process uses toluene as desorbent.

The desorption by means of this type of aromatic however, is rather slow. For the purpose of the above-mentioned application which is basically to separate a pure metaxylene vapor fraction, toluene is more suitable since it has affinity for the zeolite that is intermediate between that of the metaxylene and that of the ethylbenzene ones. Paraxylene however, is hardly displaced by toluene. Therefore, there must be used large quantities of toluene during the desorption process to make the removal complete.

SUMMARY OF THE INVENTION

The object of this invention is to carry out an industrial process that allows the separation into single components of $C_8$ aromatic hydrocarbon mixtures.

This invention solves the problem of furnishing a process for separating quickly and, in a selective way, the component being adsorbed on the zeolite material without using excessive quantities of desorbent.

These and other objects can be attained by the process of the invention by separating the aromatic hydrocarbons mixtures into the individual components by passing the mixture in vapor phase onto an adsorption bed formed by a potassium-exchanged Y zeolite which has been previously saturated by desorbent in the vapor state. The process is substantially characterized by the fact that the desorbent is isopropylbenzene, the zeolite material bed is kept at a temperature between 152.5° and 250° C. inclusive, the zeolite bed is treated during the desorption phase with an isopropylbenzene feed in vapor state which separates the pure components fractions, with the exception for the presence of the desorbent and fractions composed of mixtures of two or more of said components in the presence of the desorbent.

According to another characteristic of this invention, the fractions being desorbed from the zeolite material bed are enriched mostly in the paraxylene component which separates quickly together with the other components into cuts whose molar fraction of paraxylene is predominantly higher compared to that of the other components in the mixtures.

The zeolite used in this invention is in the form of extruded granules in which the sodium ions are fully exchanged with potassium. Furthermore, the zeolite material bed is saturated by isopropylbenzene in vapor state.

The operative conditions are as follows:

A temperature higher than or equal to the boiling temperature of isopropylbenzene at the process pressures, usually not higher than 250° C. and preferably equal to 170° C.;

pressure not higher than 2 atm, preferably at atmospheric desorbent pressure;

feed velocity on the zeolite bed between 100 and 350 $h^{-1}$.

The selectivity values as obtained for the adsorption of the various xylenes in vapor state on the zeolite saturated with isopropylbenzene, in comparison with metaxylene and measured at 170° C., are as follows:

TABLE 1

| Component | Selectivity |
|---|---|
| Orthoxylene | 1 |
| Paraxylene | 2.4 |
| Ethylbenzene | 1.6 |

The desorbent is isopropylbenzene which as, hereinbefore described, is also used to saturate, in vapor phase, the adsorbent bed before the mixture is fed thereto. The action of the desorbent is to remove the adsorbed components on the zeolite, enriching the top mixture of the component that has a lower affinity for the zeolite and that emerges from the column at a concentration which is a little higher than the one it had during the feed.

The isoprpylbenzene used in this invention during the desorption allows separation of all the components of the mixtures in the pure state more rapidly compared to the conventional processes (which require the intervention of recycles or other auxillary operations) without utilizing an excess of desorbent.

Unlike the traditional processes, the xylene-fractions produced according to this invention increasingly are enriched in the individual components, inlcuding paraxylene that is present with higher molar fractions in the cuts separated by desorption.

The enrichment of paraxylene in the vapor stream emerging from the column in the desorption phase, which enrichment reaches almost unitary molar fractions, would not be possible, if the desorption were made using toluene or other aromatic derivatives instead of isopropylbenzene.

Example 6 clearly shows this difference in the separation results. From these results it may be observed that, in spite of what would have been expected, the choice of the desorbent affects the type and the quality of the desorbed fractions and it is noticed especially that isopropylbenzene is more active as desorbent compared to those used in the traditional processes there being lower either the time necessary to let all the components emerge, or the quantity of the desorbent necessary so that it can take place.

The above effect clearly results from the desorption curves of the attached figures of the drawing which represent the component molar fraction that is obtained at the outlet of the column depending on the time and on the quantity of desorbent as fed, i.e., isopropylbenzene. Of especial interest the comparison between the desorption curves of FIGS. 8 and 11, both referred to the meta/paraxylene separation respectively carried out with isopropylbenzene and toluene. After checking these figures, it is confirmed, among other things, that the separation of paraxylene occurs with concentration levels notably higher in the case of isopropylbenzene, and a higher rate by which such a separation takes place. Such higher rates means that lower total amounts of the desorbent are required. Without limiting this invention, it seems plausible that this phenomenon is because of the fact that isopropylbenzene presents a higher affinity against the zeolite compared to the other types of desorbent presently being used.

According to the conditions, it is possible to operate in different ways. For instance, it is possible to feed quantities of xylenes lower than the load capacity of the zeolite by using the desorbent as a fluid carrier. In this way one may obtain an almost complete separation between meta and paraxylene. This can be seen from example 4, where there is also shown the effect of the variations of the linear rate of the desorbent feeding to the separation.

Figure 9:
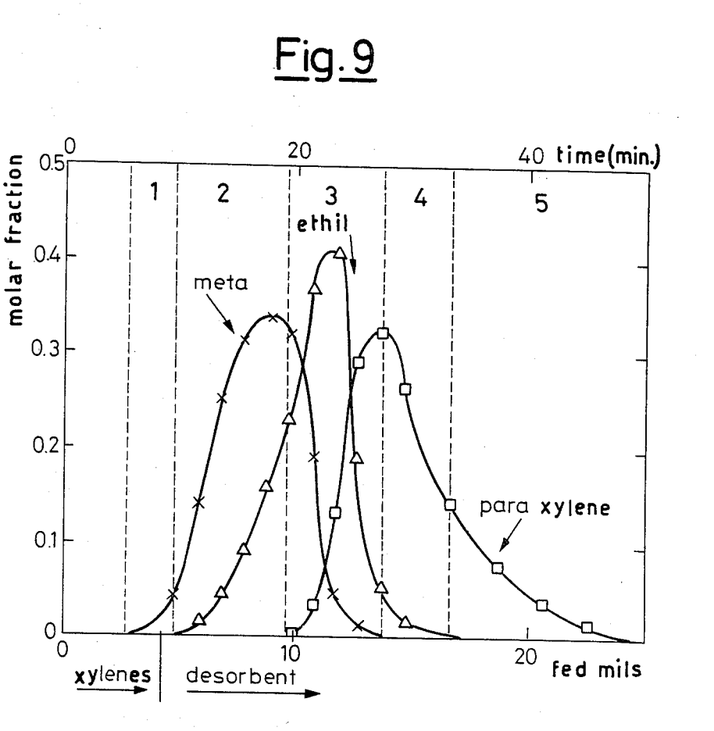

By increasing the length of the columns at the same diameter as shown on the desorption curves on FIG. 9 bis, there can be observed the complete separation of the fractions of the pure components, except for the desorbent which is still present.

In the following examples, reference is made to different adsorption and desorption curves, experimentally obtained by using for the analysis the vapor flowing out from the column and a gas chromatograph mounted on line and equipped with an automatic sampling valve kept at the temperature of the column.

DETAILED DESCRIPTION

Example 1

Breakthrough curves either in adsorption or in desorption for a binary mixture of metaxylene and paraxylene (1:1 in moles) using isopropylbenzene as desorbent. The column used is made of copper, has a diameter of 1 cm and a length of 1 m. It contains 54.26 g of potassium-exchanged zeolite pretreated as described above. In the adsorption test, a mixture containing 50% in moles of the two isomers, i.e. metaxylene and paraxylene was fed, after vaporisation, at atmospheric pressure, on the adsorbent bed kept at 170° C. with a load of 0.25 cm$^3$/min. of liquid at 25° C. The adsorbent bed was previously saturated with isopropylbenzene.

Figure 1:
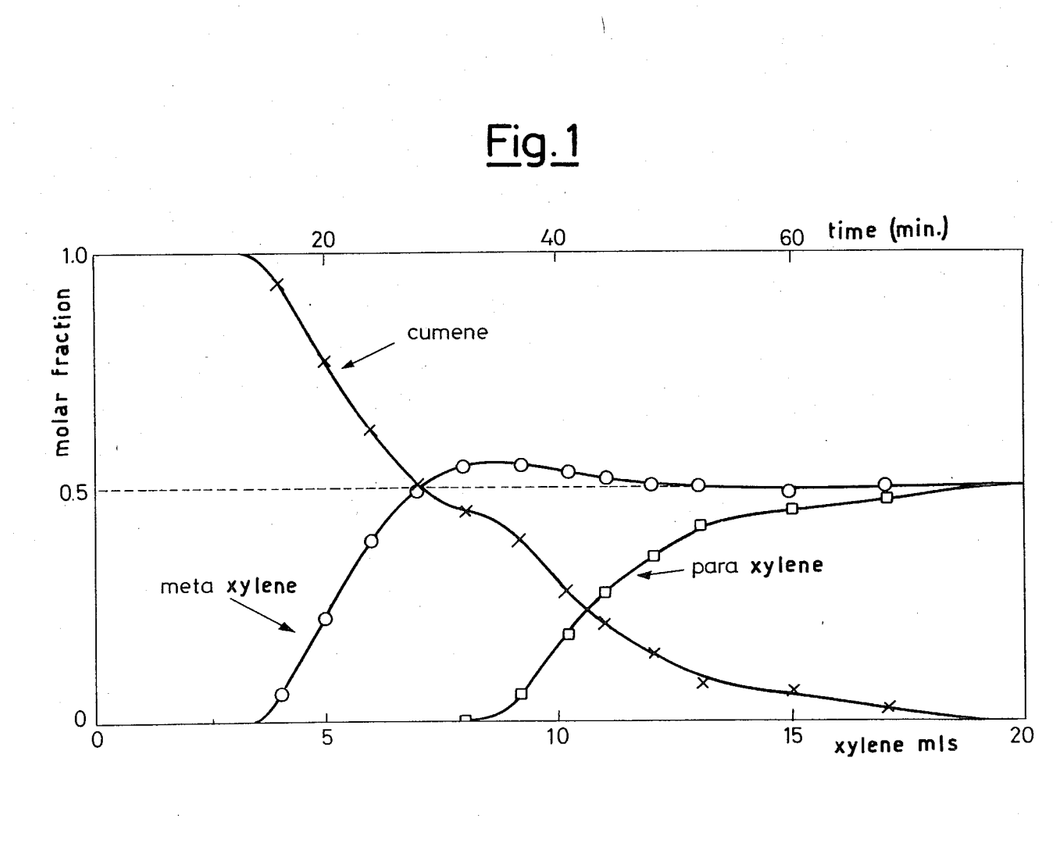
FIGS. 1 and 2 depict the breakthrough curves during the separation of meta/paraxylenes using isopropylbenzene (cumene) as a desorbent.

The breakthrough curves of FIG. 1 were obtained. From these curves it can be seen that the quantities of meta and paraxylene adsorbed were respectively $3.5 \times 10^{-4}$ moles/g and $8.4 \times 10^{-4}$ moles/g.

The selectivity values are shown in Table 1. The quantity of metaxylene that is fully separated from paraxylene represents about 35% by weight in comparison to that fed up to that stage.

Figure 2:
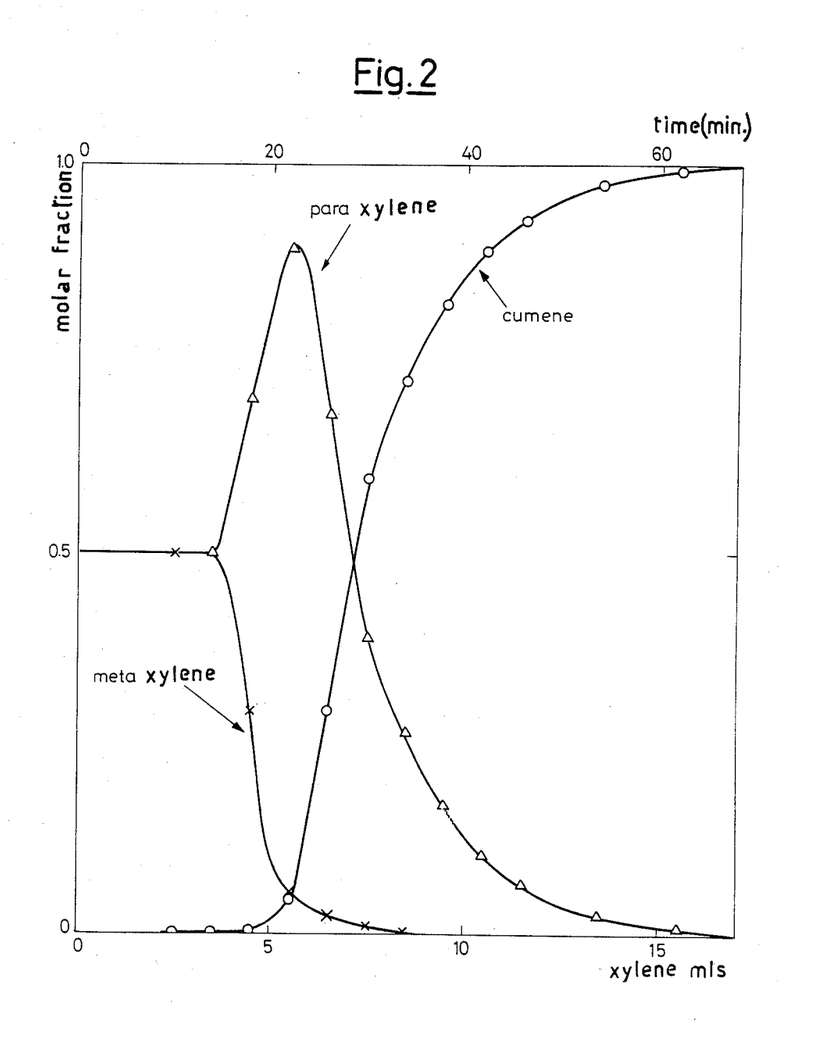

When the adsorbent bed reached equilibrium, i.e. at the end of the adsorption test, the desorption process was started with isopropylbenzene, always in vapor phase and at the same temperature of 170° C., with the same load of 0.25 cm$^3$/min. Metaxylene and paraxylene came out as seen in FIG. 2.

From these curves there can be obtained the desorbed amounts of meta and paraxylene which coincide with those obtained in the adsorption phase. Clearly there is confirmed the selectivity obtained from these tests.

The zeolite load capacity is equal to about $1.2 \times 10^{-3}$ moles of xylene/g. Upon examination of the breakthrough curve, obtained in the desorption phase, it is seen that the paraxylene comes out at a concentration which is higher than that of equilibrium corresponding to a molar fraction of 0.5.

During this phase there is an enrichment in paraxylene in the outflowing mixture in accordance with a phenomenon that is typical of the displacement chromatography. The amount of paraxylene fully separated from metaxylene represents about 10% by weight compared to the whole desorbed paraxylene.

Example 2

Figure 3:
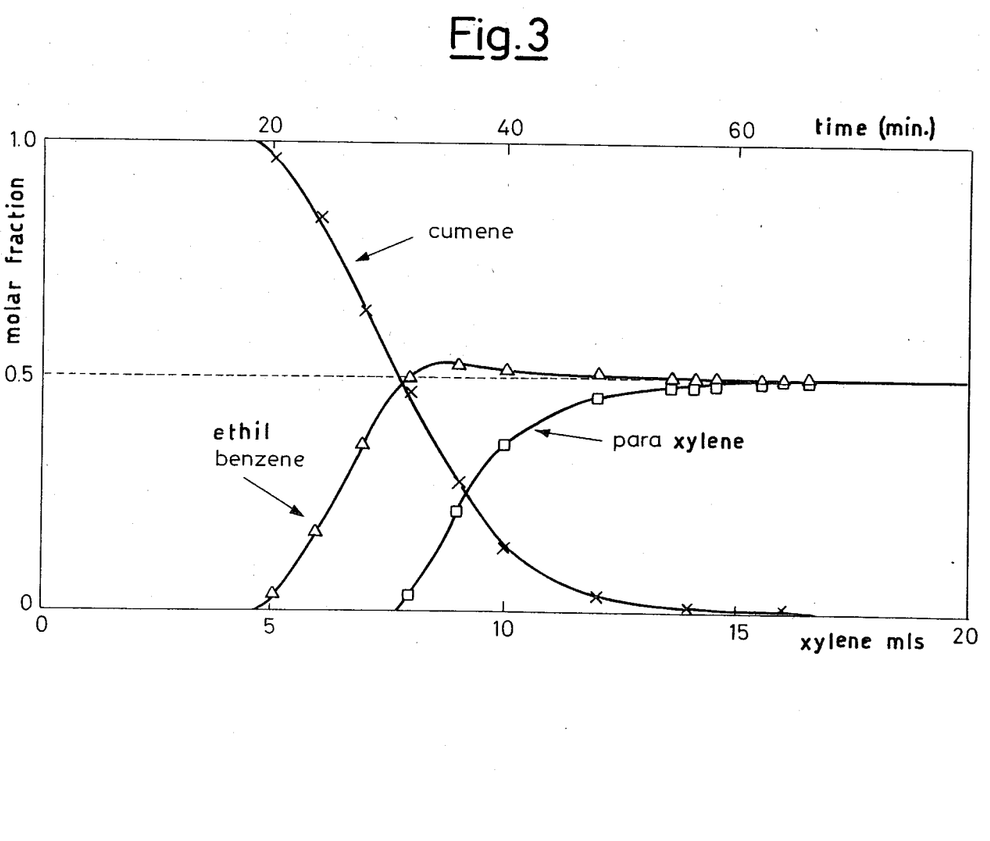
FIGS. 3 and 4 show the breakthrough curves during the separation of ethylbenzene and paraxylene using isopropylbenzene as a desorbent.
Figure 4:
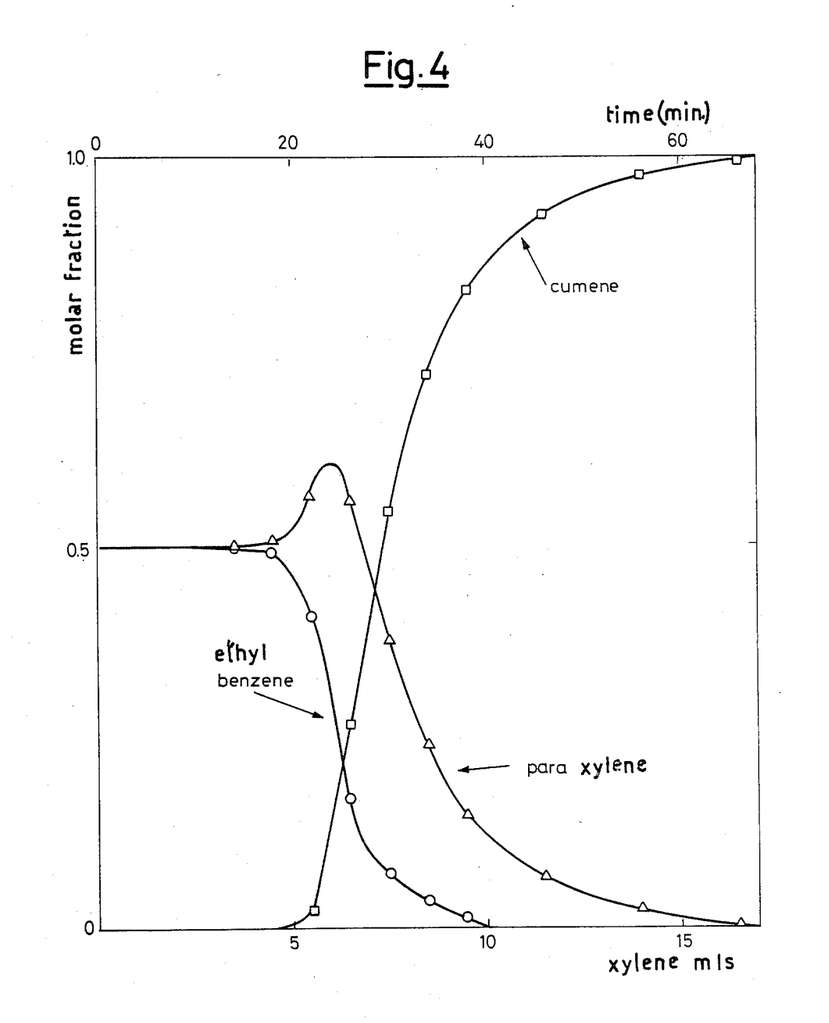

Breakthrough curves either in adsorption or in desorption for a binary mixture of ethylbenzene and paraxylene (1:1 in moles), using isopropylbenzene as desorbent. The column is the same as described in example 1. The operating temperature and the loads were also equal. The breakthrough curves obtained in the adsorption step are shown in FIG. 3. Those in the desorption phase with isopropylbenzene are illustrated in FIG. 4. From both graphs it is possible to obtain the amounts of the adsorbed ethylbenzene and paraxylene, the average amount respectively being $4.6 \times 10^{-4}$ moles/g and $7.2 \times 10^{-4}$ moles/g. The amount of ethylbenzene fully separated from paraxylene in the adsorption phase represents a weight of about 15% in comparison to the ethylbenzene fed up to that point.

The amount of paraxylene fully separated in the desorption phase represents about 5.5% by weight of the desorbed total mixture.

In this case also, as in the previous example, there is obtained an enrichment of the paraxylene in the desorption phase in comparison to the equilibrium compositions. The load capacity of zeolite is confirmed.

Example 3

Figure 5:
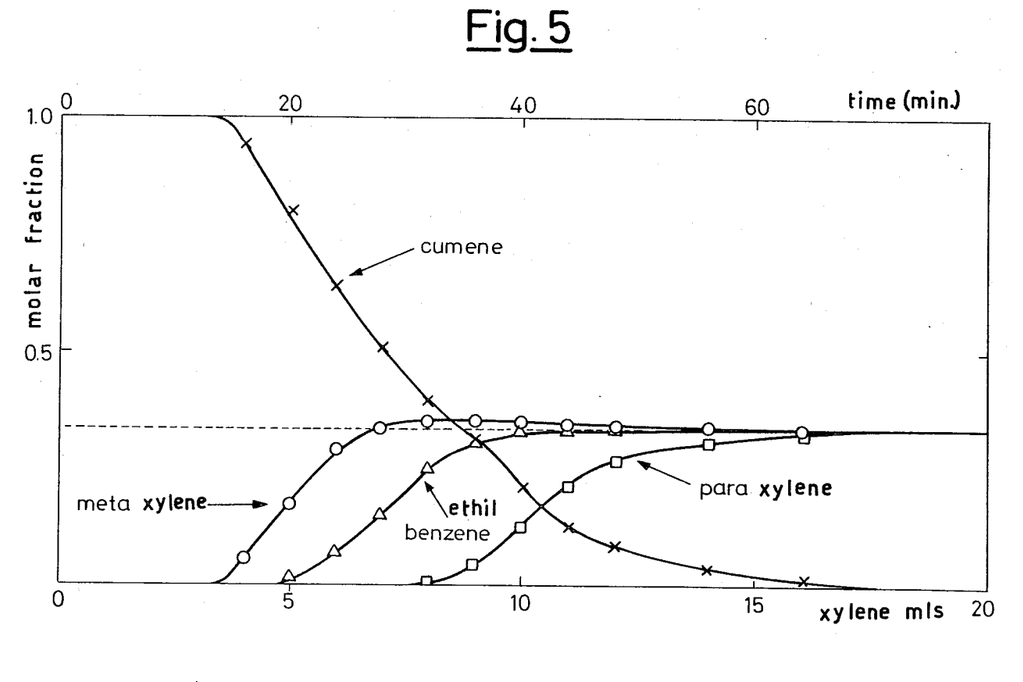
FIGS. 5, 6, 9, 9 BIS and 10 illustrate various breakthrough curves during the separation of a ternary mixture of metaxylene, ethylbenzene, and paraxylene using isopropylbenzene as a desorbent.
Figure 6:
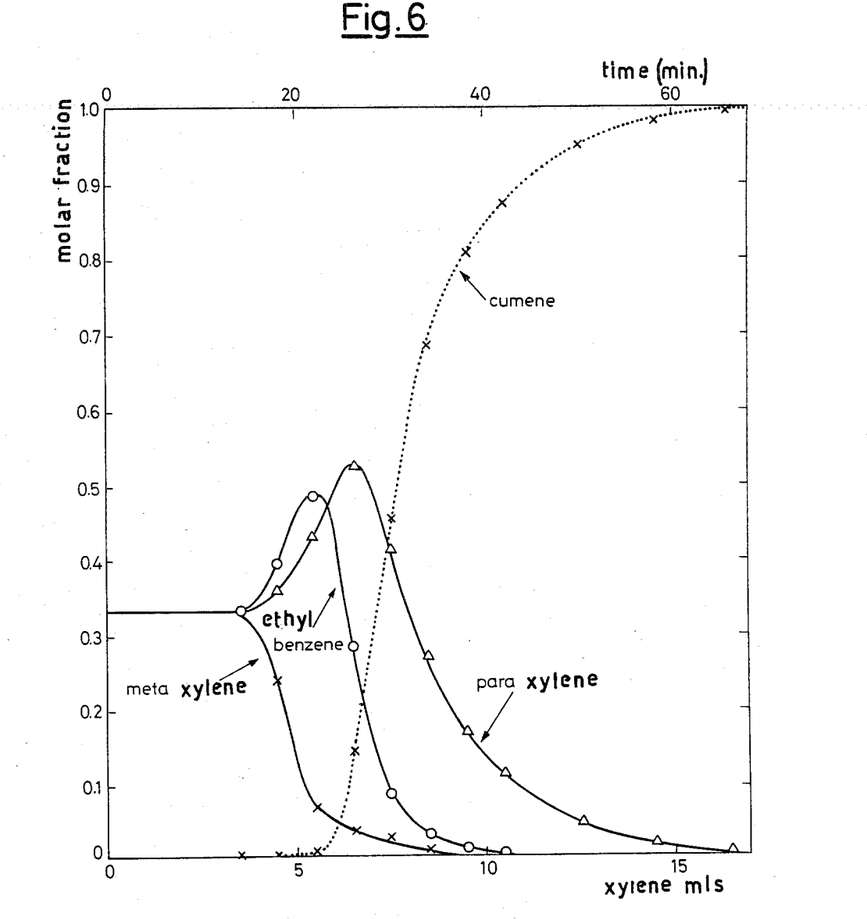

Breakthrough curves either in the adsorption or the desorption phase for metaxylene, ethylbenzene and paraxylene ternary mixtures (1:1:1 in moles) using isopropylbenzene as desorbent. The column and the operational conditions are the same as in the previous examples. The breakthrough curves obtained in the adsorption phase for the three components are shown in FIG. 5, while those obtained for the desorption phase are shown in FIG. 6.

The amounts adsorbed which can be obtained from the two graphs on an average are $2.3 \times 10^{-4}$ moles/g of metaxylene, $3.6 \times 10^{-4}$ moles/g of ethylbenzene and $5.4 \times 10^{-4}$ moles/g of paraxylene.

Therefore the selectivity data of Table 1 and the zeolite total load capacity are confirmed again.

The metaxylene fully separated in the adsorption phase represents 3.2% of that fed at that stage.

It can be seen from the adsorption curves how two fractions comprising (1) metaxylene plus desorbent and (2) metaxylene plus ethylbenzene, the compositions of which are reported in Table 2, can be separated.

Also, from the desorption curves, it can be seen how it should be possible to recover about 7.5% by weight of paraxylene in comparison to all of the desorbed paraxylene by means of a composition, which composition is also shown in Table 2.

Composition of the fractions that can be separated in the breakthrough curves for three components:

|  | Metaxylene | ethyl-benzene | paraxylene | Desorbent |
|---|---|---|---|---|
| 1st Fraction (adsorption) | 3.7 | | | 96.3 |
| 2nd Fraction (adsorption) | 25.1 | 7.7 | | 67.2 |
| 3rd Fraction (desorption) | | | 3.8 | 96.2 |

If columns having a length of 4 m of the same diameter and at the same conditions as in example of FIG. 9 are used, the separation shown in FIG. 9 Bis is obtained, from which it can be seen how it should be possible to separate fractions of the three components which are pure except for the desorbent.

Example 4

Separation of meta and paraxylene binary mixtures (1:1 in moles) by feeding amounts of xylenes lower than the zeolite load capacity, using the desorbent as fluid carrier, at different loads.

The test always were carried out in the same column and at the same temperatures and pressures. There were sent onto the zeolite bed saturated with isopropylbenzene 4 cm$^3$, measured at 25° C., of the mixture having a molar ratio 1:1 of meta and paraxylene with a load of 0.206 cm$^3$/min. The desorbent, isopropylbenzene always was passed with the same load on the xylenes being fed.

Figure 7:
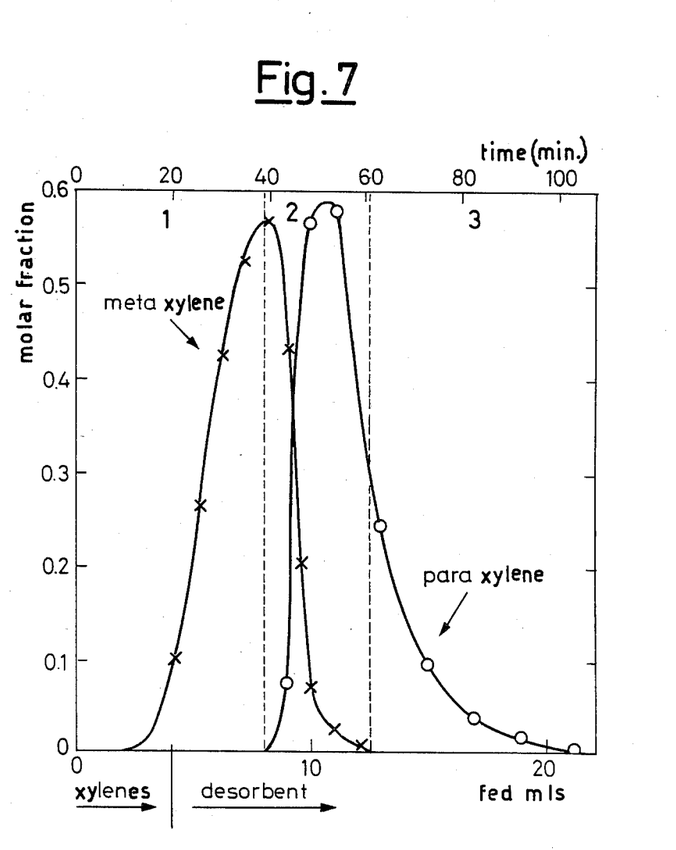
FIGS. 7 and 8 depicts the breakthrough curves during the separation of meta/paraxylene employing isopropylbenzene as a desorbent.

In FIG. 7 there is shown how under the described conditions, meta and paraxylene may flow out in almost completely separated manner.

Figure 8:
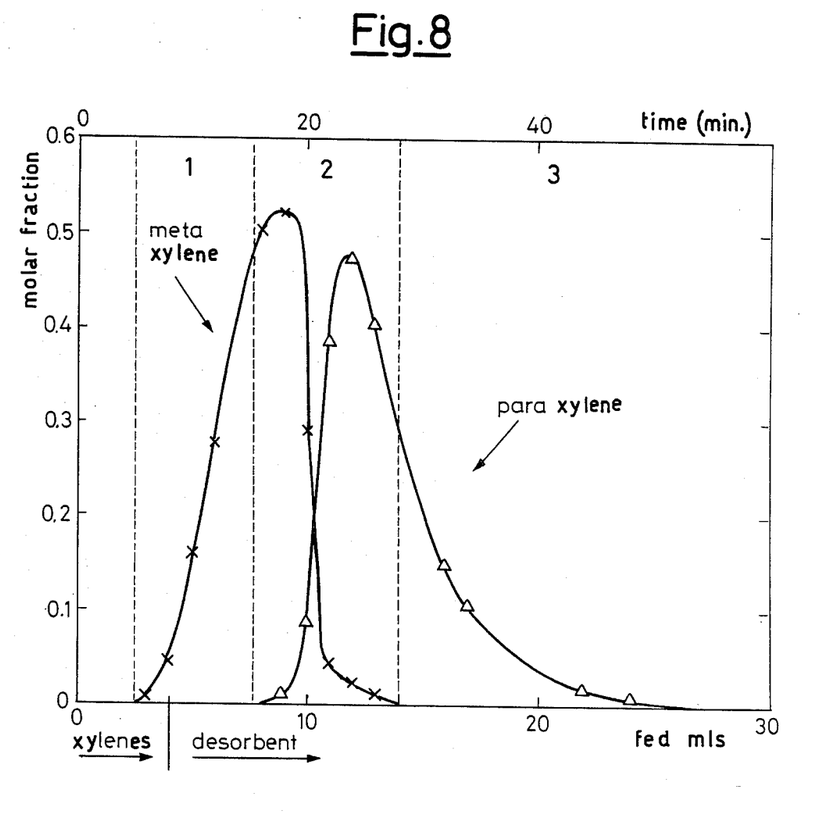

A test fully similar to the previous one, except for the load either of xylene or of desorbent which was kept to 0.5 cm$^3$/min, gave the results that can be seen on FIG. 8.

As can be observed, by increasing the linear velocity the duration of the experiment decreases but the amount of the desorbent used increases and the separation decreases.

By carrying out the separation in this way, three fractions are obtained as shown by the dashed curves in the figures.

The compositions of these fractions as set forth in Table 3, confirm the previous observations. For a good separation it is suitable, therefore, to operate with space velocities between 30 and 600 h$^{-1}$ valves between 100 and 350 h$^{-1}$ are preferred.

TABLE 3

| | Fraction 1 | | | Fraction 2 | | | | Fraction 3 | | |
|---|---|---|---|---|---|---|---|---|---|---|
| | | Distribution | | | Distribution | | | | Distribution | |
| Load (cm$^3$/m$^1$) | % on total | meta % | Des. % | % on total | m % | p % | d % | % on total | para % | des. % |
| 0.205 | 30 | 28 | 72 | 23 | 18.4 | 36 | 45.6 | 47 | 7 | 93 |
| 0.5 | 22 | 18.7 | 81.3 | 28 | 19.7 | 24.2 | 56.1 | 50 | 7 | 93 |

Example 5

Separation of ternary mixtures of metaxylene, ethylbenzene and paraxylene (1:1:1 in moles) by feeding xylene amounts lower than the zeolite load capacity and by using the desorbent as fluid carrier.

The column was the same one used in the previous examples, and the temperatures and pressure operational conditions remained unchanged.

In a first test 4.5 cm$^3$ of the xylene mixture (metaxylene, paraxylene, ethylbenzene 1:1:1 in moles) were passed with a load of 0.5 cm$^3$/min on the already saturated isopropylbenzene.

After the feed of xylenes was terminated isopropylbenzene was sent as fluid carrier having the same load. The merging peaks have a shape that can be seen in FIG. 9. It confirmed that, at the described conditions, meta and paraxylene are almost completely separated.

In a further test, under identical conditions, 9 cm$^3$ of xylenes were fed instead of 4.5 cm$^3$. The results obtained are reported in FIG. 10.

As can be seen, the separation of the different components is very satisfactory.

Figure 10:
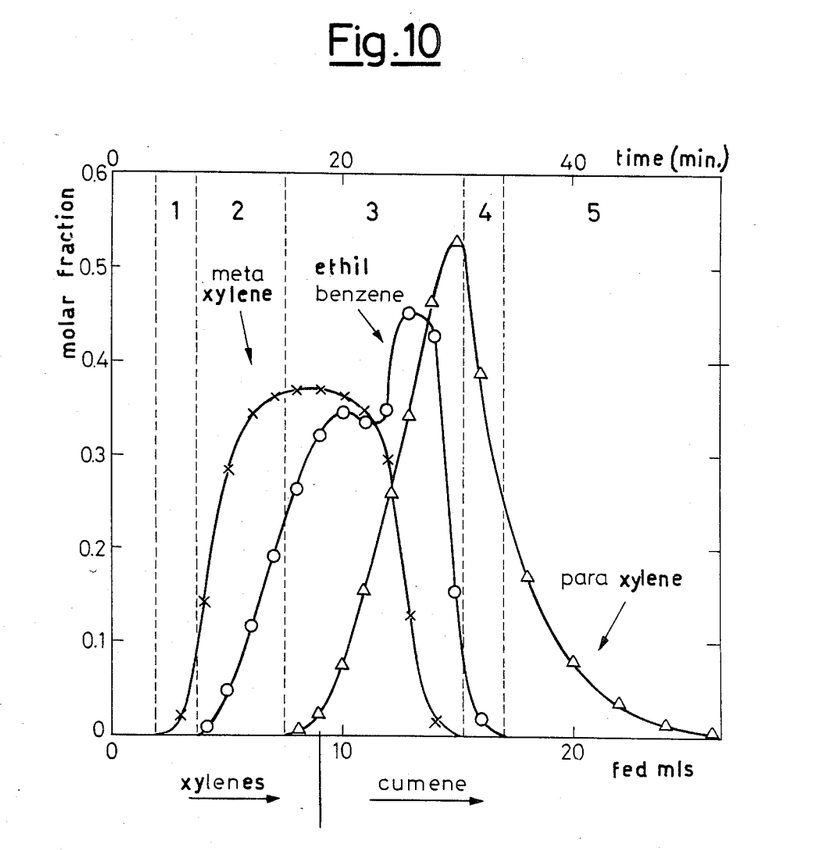

From FIGS. 9 and 10 it can be seen how it is possible to separate, as was effectively carried out, five fractions. This is shown by dashed lines in the figures which have the compositions reported in Table 4. The data of this table confirm the possibility of obtaining fractions containing pure metaxylene (fraction 1) and paraxylene (fraction 5), except for the presence of desorbent, together with fractions enriched in the same components (fractions 2, 3, and 4).

TABLE 4

Composition of the fractions obtained in the test of FIGS. 9 & 10

| | Fraction 1 | | | Fraction 2 | | | | Fraction 3 | | | | |
|---|---|---|---|---|---|---|---|---|---|---|---|---|
| | | Distribution | | | Distribution | | | | Distribution | | | |
| Fed xylenes | % on total | m % | des. % | % on total | m % | e % | des. % | % on total | m % | e % | p % | des. % |
| 4.5 | 9 | 2 | 98 | 22 | 23.4 | 7.3 | 69.3 | 19 | 10.1 | 25.4 | 14.8 | 49.7 |
| 9 | 7 | 3.2 | 96.8 | 15 | 29.1 | 9.7 | 61.2 | 32 | 24.3 | 33.3 | 22.4 | 20 |

| | Fraction 4 | | | | Fraction 5 follows | | |
|---|---|---|---|---|---|---|---|
| | | Distribution | | | | Distribution | |
| Fed xylenes | % on total | e % | p % | des. % | % on total | p % | des. % |
| 4.5 | 14 | 1.3 | 20.4 | 78.3 | 36 | 4.7 | 95.3 |
| 9 | 8 | 3 | 35 | 62 | 38 | 6.5 | 93.5 | m = Methylene;
p = Paraxylene;
e = Ethylbenzene;
Des. = Desorbent.

As a final point, the amount of xylenes fed by following the above-mentioned procedure, can be increased to completely fill the bed, the zeolite load capacity being well known.

Example 6

Comparison between the isopropylbenzene desorbent effect and that of other desorbents, especially toluene.

In this case a test was made for the separation of a binary mixture formed of meta and paraxylene (1:1 in moles) by feeding, as in example of FIG. 8, 4 cm³ of such a mixture on the previously described column and with the same operative conditions of temperature and pressure, using a load of 0.5 cm³/min, the adsorbent bed being saturated with toluene. After feeding of the xylenes was terminated, toluene was fed as fluid carrier, always at a load of 0.5 c³/min.

Figure 11:
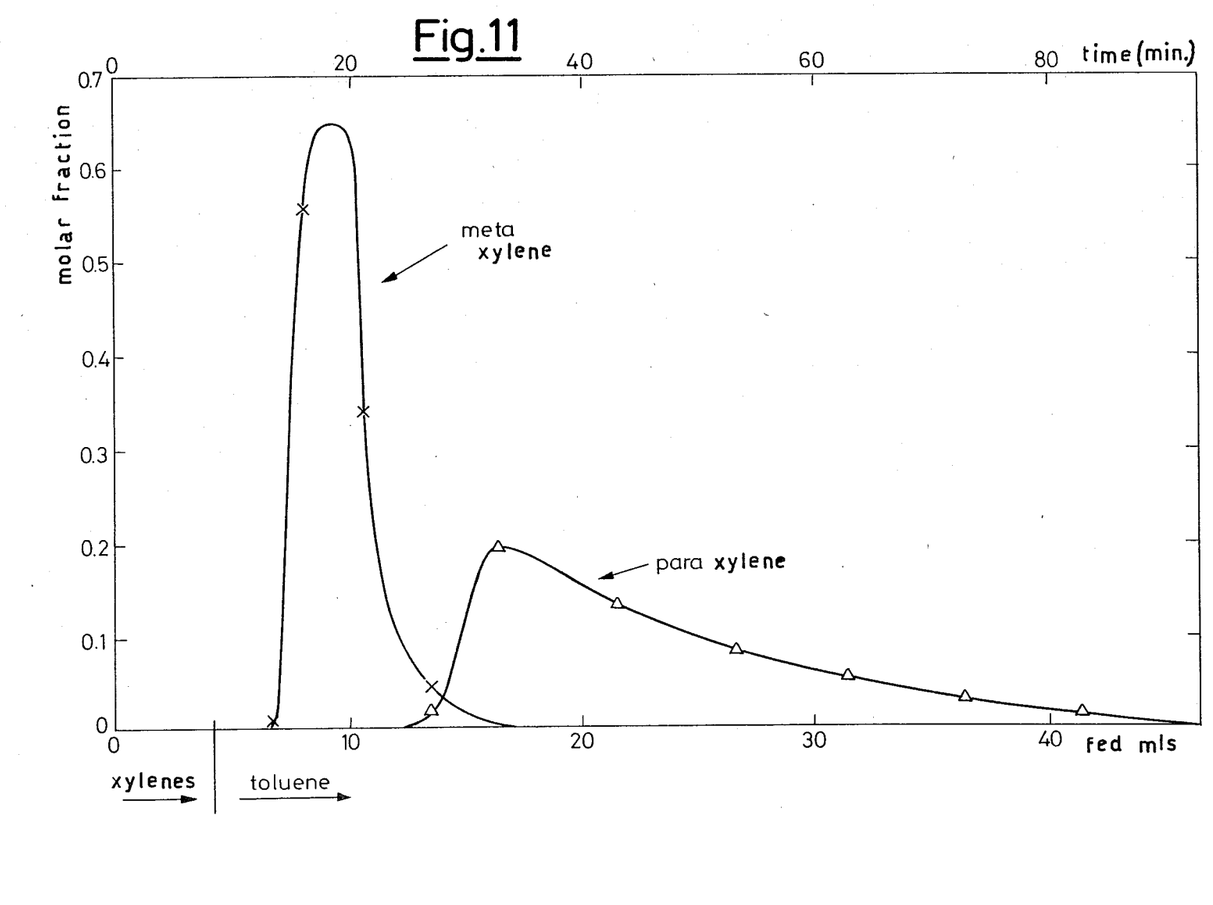
FIG. 11 illustrates the breakthrough curves during the separation of meta/paraxylene employing toluene as a desorbent.

The emerging peaks have the shape shown on FIG. 11. If there is compared this figure with the one for the test of FIG. 8 carried out with isopropylbenzene as desorbent, it can be seen that isopropylbenzene is more efficient as a desorbent, being lower either in the required time to let both components come out or in the required amounts of the desorbent.

On the other hand, the separation is not appreciably decreased, the selectivity remaining the same.

Tests also have been made with other desorbents, as for instance benzene, and the reaction is poorer in comparison with toluene; aromatic components having higher molecular weight than cumene also have been tested with good results in regard to the desorbent capacity; however, as they require a further increased temperature, they cause a lowering in the load capacity of the zeolite and in the separations effected thereby, i.e. in selectivity.

We claim:

1. In a process for the separation of an aromatic hydrocarbon mixture into its single components through passage of the mixtures in the vapor phase on an adsorption bed formed of a potassium-exchanged Y zeolite, the latter being previously saturated by desorbent vapor, said aromatic hydrocarbon mixture containing either at least two xylenes or at least two xylene and ethyl benzene, the improvement comprising employing isopropylbenzene as the desorbent keeping the zeolite material bed at a temperature between 152.5° C. and 250° C., including treating the zeolite bed during the desorption phase with a feed of isopropylbenzene in the vapor phase which separates fractions of the pure components except for the presence of the desorbent and fractions formed of mixtures of two or more of said components in presence of the desorbent, the amount of desorbent required to effect said separation being less than the amount of toluene required to give the same separation.

2. A process according to claim 1, wherein the operating pressure of the vapors on the zeolite bed is atmospheric pressure and that the space velocity of the feeding of isopropylbenzene on the same zeolite bed is between 100 and 350 h$^{-1}$.

3. A process according to claim 2, wherein the aromatic hydrocarbon mixture contains paraxylene, wherein the operating pressure of the vapors on the zeolite bed is the atmospheric pressure and that the space velocity of the feeding of isopropylbenzene on the same zeolite bed is of between 100 and 350 h$^{-1}$.

4. A process according to claim 2, wherein the operating temperature of the zeolite bed is 170° C.

5. A process according to claim 2, wherein in the adsorption step, a mixture of xylenes except for orthoxylene is fed on the zeolite bed until equilibrium is obtained a first fraction containing metaxylene and desorbent and a second fraction containing metaxylene, ethylbenzene and desorbent being separated; while in the desorption step, in which the zeolite bed is treated with an equivalent load of isopropylbenzene, a fraction containing paraxylene and desorbent, as well as fractions formed of mixtures of the xylenes and the desorbent predominantly rich in paraxylene is collected.

6. A process according to claim 1 comprising feeding the xylene mixture in a lower quantity than that needed to saturate the adsorption bed, and in the desorption phase with isopropylbenzene, collecting the individual components which are pure for the desorbent, and also collecting mixtures of the components predominantly richer in paraxylene than the starting mixture.

7. A process according to claim 6, wherein a metaxylene, ethylbenzene and paraxylene ternary mixture is fed in lower quantity than that necessary to saturate the zeolite bed, and in that in the desorption phase five fractions are obtained, the first and the last of which contain only metaxylene and desorbent and respectively metaxylene and desorbent, the three intermediate fractions being formed of xylene mixtures in the presence of desorbent.

8. A process according to claim 7, wherein fractions of the three pure components, except for the desorbent, are further separated.

* * * * *